United States Patent
Zhang et al.

(10) Patent No.: US 10,682,038 B1
(45) Date of Patent: Jun. 16, 2020

(54) AUTONOMOUS ROBOTIC LAPAROSCOPE BASED ON EYE TRACKING

(71) Applicant: Colorado School of Mines, Golden, CO (US)

(72) Inventors: Xiaoli Zhang, Arvada, CO (US); Songpo Li, Golden, CO (US)

(*) Notice: Subject to any disclaimer, the term of this patent is extended or adjusted under 35 U.S.C. 154(b) by 40 days.

(21) Appl. No.: 14/860,696

(22) Filed: Sep. 21, 2015

Related U.S. Application Data

(60) Provisional application No. 62/052,931, filed on Sep. 19, 2014, provisional application No. 62/052,900, filed on Sep. 19, 2014.

(51) Int. Cl.
| | | |
|---|---|---|
| *G06F 3/01* | (2006.01) | |
| *A61B 1/00* | (2006.01) | |
| *A61B 1/313* | (2006.01) | |
| *A61B 1/04* | (2006.01) | |
| *A61B 19/00* | (2006.01) | |
| *A61B 17/00* | (2006.01) | |

(52) U.S. Cl.
CPC ...... *A61B 1/00006* (2013.01); *A61B 1/00149* (2013.01); *A61B 1/00188* (2013.01); *A61B 1/04* (2013.01); *A61B 1/3132* (2013.01); *A61B 2017/00216* (2013.01); *A61B 2019/2211* (2013.01)

(58) Field of Classification Search
CPC .. G06F 3/013; G06F 3/012; G01B 2027/0187
See application file for complete search history.

(56) References Cited

U.S. PATENT DOCUMENTS

| | | | | |
|---|---|---|---|---|
| 5,689,619 | A * | 11/1997 | Smyth | G02B 27/0093 345/156 |
| 8,885,882 | B1 * | 11/2014 | Yin | G06F 3/00 382/103 |
| 10,157,313 | B1 | 12/2018 | Zhang et al. | |
| 2010/0226535 | A1 | 9/2010 | Kimchi et al. | |

(Continued)

OTHER PUBLICATIONS

Abbott et al., "Ultra-low-cost 3D gaze estimation: an intuitive high information throughput compliment to direct brain-machine interfaces," Journal of Neural Engineering, 2012, pp. 1-11, vol. 9.

(Continued)

*Primary Examiner* — Alexandra L Newton
(74) *Attorney, Agent, or Firm* — Dorsey & Whitney LLP

(57) ABSTRACT

The presently disclosed devices, methods, and systems involve direct and intuitive visualization using gaze-control in robotic laparoscopy. For example, when the system detects a new visual interest, the robot may guide the scope to approach or move toward the target view. In order to achieve the disclosed control, a system coordinate transformation is developed. The disclosed devices, methods, and systems may translates gaze positions on image (in pixels) to relative rotation angles and/or translation distances of the laparoscope. In most cases, this relationship, which may be built, in part, on the parameters of the laparoscope and the inserted laparoscope length in the patient's body, may allow the robot to directly follow the surgeon's gaze position on the monitor. The disclosed devices, methods, and systems may help to reduce cognitive and physical burdens on a laparoscopic surgeon.

9 Claims, 9 Drawing Sheets

(56) References Cited

U.S. PATENT DOCUMENTS

| | | |
|---|---|---|
| 2010/0321482 A1 | 12/2010 | Cleveland |
| 2011/0228975 A1 | 9/2011 | Hennessey et al. |
| 2012/0069166 A1* | 3/2012 | Kunz .................. A61B 1/00039 348/65 |
| 2012/0133754 A1* | 5/2012 | Lee .......................... G06F 3/013 348/78 |
| 2013/0050432 A1 | 2/2013 | Perez et al. |
| 2014/0024889 A1* | 1/2014 | Xiaoli ................. A61B 1/00039 600/102 |
| 2014/0300538 A1 | 10/2014 | Rijnders et al. |
| 2016/0018639 A1 | 1/2016 | Spitzer et al. |
| 2016/0085299 A1* | 3/2016 | Horesh ................... G06F 3/013 345/156 |
| 2016/0086338 A1* | 3/2016 | Nagamatsu ............... G06T 7/80 348/78 |

OTHER PUBLICATIONS

Hennessey et al., "Noncontact Binocular Eye-Gaze Tracking for Point-of-Gaze Estimation in Three Dimensions," IEEE Transactions on Biomedical Engineering, Mar. 2009, pp. 790-799, vol. 56, No. 3.
Lee et al., "3D gaze tracking method using Purkinje images on eye optical model and pupil," Optics and Lasers in Engineering, 2012, pp. 736-751, vol. 50.

* cited by examiner

AUTONOMOUS ROBOTIC LAPAROSCOPE BASED ON EYE TRACKING

CROSS REFERENCE TO RELATED APPLICATIONS

This application claims benefit of priority pursuant to 35 U.S.C. § 119(e) of U.S. provisional patent application Nos. 62/052,931 and 62/052,900 filed Sep. 19, 2014 both of which are hereby incorporated by reference in their entirety.

FIELD

The disclosed processes, methods, and systems are directed to control of robotic devices, such as robotic laparoscope devices, based on tracking the visual interest of a user on a robotic device's display.

BACKGROUND

The patent or application file contains at least one drawing executed in color. Copies of this patent or patent application publication with color drawing(s) will be provided by the Office upon request and payment of the necessary fee.

Most current input controls, for example joysticks, voice commands, and gesturing, require the user to locate a point of visual interest on a screen with their eyes. Thus, a user must first identify a view of interest for the robotic device. The user must then formulate appropriate decisions to yield motor responses (through fingers, hands, arms, legs, or speech) to change a particular field of view (FOV) of the robotic device. In most cases, these controls require multi-body-part coordination to manipulate the robotic device, such as a laparoscope, which creates a barrier between the surgeon and the surgical site. Other previous robotic control devices used voice control to effect change in the robotic device. However, studies have demonstrated that voice control is less efficient than a practiced and attentive human assistant.

Fundamentally, the eye is a perceptual organ not meant for an output communication channel. Therefore, using solely gaze as a control input signal requires the differentiation of normal behavioral eye movements and intentional eye "commands," which is known as the Midas touch problem (the eyes cannot be used directly as a mouse, because the eyes are never "off.") The "select" or "click" command is usually derived from tedious eye gestures (such as excessive blinks, over-long dwell time, other controlled eye movements) as a confirmation to a specific command from the eye). Ideally, gaze-based robot control would be conducted implicitly without tedious eye gestures.

Existing gaze control modes are indirect, incremental, and offer only relative control of the robotic control (e.g., control with respect to the robot's previous position). This may cause the robotic device to effect direction/joint rotation with only one fixed step, and multiple steps of motion commands are usually needed to approach a target view. Other existing systems adopt regression-based methods, which are highly dependent on the mapping relation between eye movements and a display surface. In the case of visual control of surgical instruments and robotic devices, these methods require a surgeon's head to remain relatively still and a recalibration is needed if the user's head moves. Therefore, regression-based methods are impractical in the operating room or surgical suite as the surgeon may move his/her head and even look at other directions in activities such as tool changing, communication with other personnel, and checking other monitoring instruments (ultrasound image, heartbeat, blood pressure, etc.).

One problem inherent with known laparoscopic surgery techniques is inconvenient, limited visualization in comparison with traditional open surgery. In laparoscopic surgery, the surgeon's view is normally limited to what is in front of the scope. In many cases, the surgeon needs to frequently readjusts the laparoscope What is needed is a new type of robotic device and control system to make surgeon or other user robotic device interaction more effective and intuitive, and to make the execution of surgical maneuvers smoother and faster. Further, a system which is adaptive the movement of a user's head is desirable to enable freedom of movement. In some cases, described herein, the surgeon's control burden may be reduced by increasing the level of autonomy in the disclosed robotic device, e.g. robotic laparoscope, systems.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Disclosed herein are devices, methods, processes, and systems for gaze-based control of a robotic device. In many cases, the disclosed devices, methods, processes, and systems aid in allowing for more intuitive, effective, smoother, faster, and more autonomous control of the robot, for example a medical robotic device. In some cases the medical robot is a laparoscope, endoscope, anthroscope, or the like.

In some examples, the presently disclosed devices, methods, and systems involve direct and intuitive visualization using gaze-based control in robotic laparoscopy. For example, when the system detects a new visual interest, the robot may guide the scope to approach or move toward the target view. In order to achieve the disclosed control, a system coordinate transformation is developed. The disclosed devices, methods, and systems may transform detected gaze positions or gaze points on a display image (in pixels) to relative rotation angles and/or translation distances of the laparoscope. The transformation may be based on the parameters of the laparoscope and the inserted laparoscope length in the patient's body, and may enable the robot to directly follow the surgeon's gaze position on the monitor. Accordingly, the disclosed devices, methods, and systems may help to reduce cognitive and physical burdens on a laparoscopic or other robotic device or remote-camera device.

Figure 1:
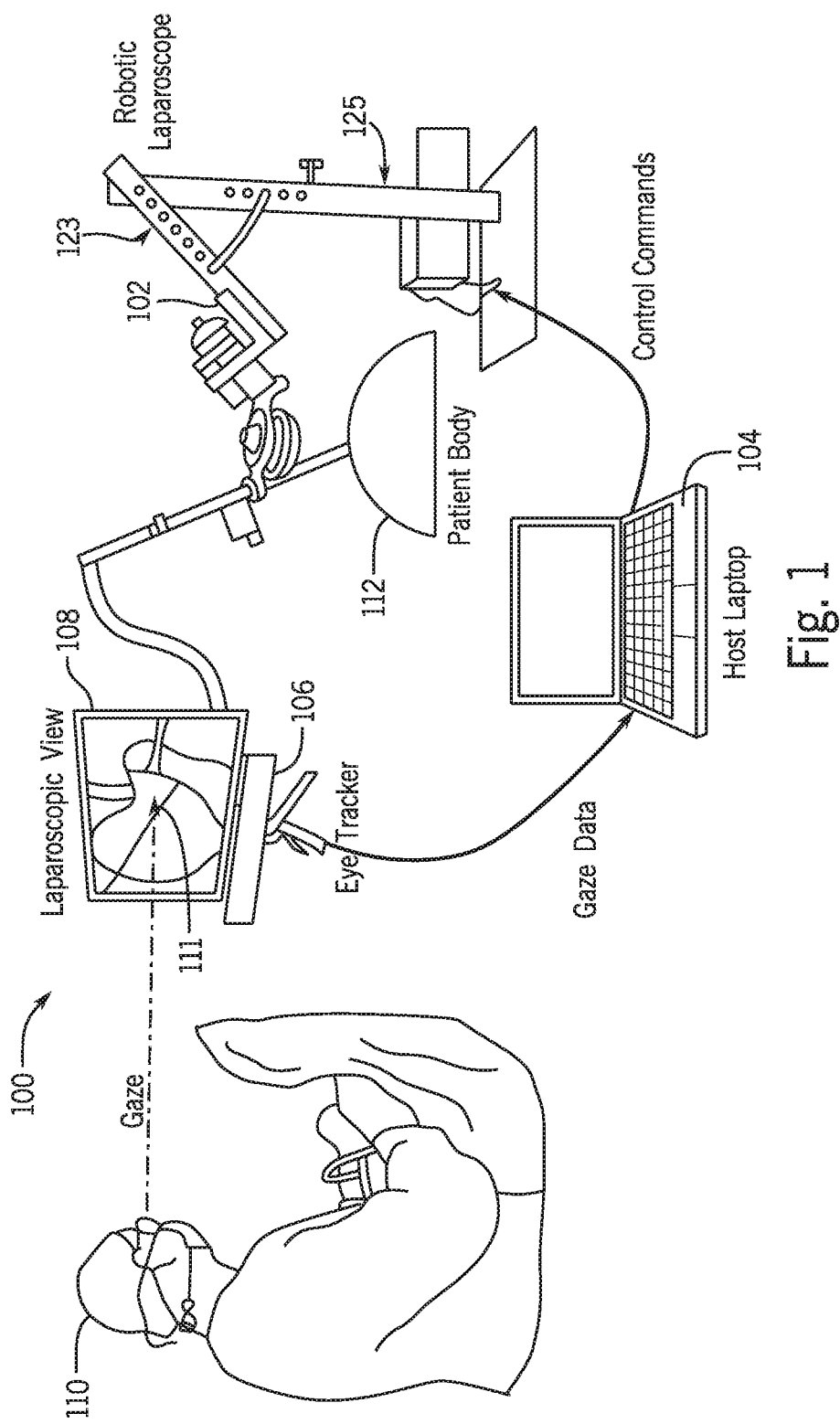
FIG. 1 is an overall system view of the robotic control system and method based on eye tracking.

Turning now to the drawings, FIG. 1 depicts an exemplary schematic view of the robotic device control system 100 and method. In some examples, the robotic device 102 may be a surgical robotic device 102 such as laparoscope, endoscope, or the like. A user 110, such as a surgeon, may view the robotic device's 102 display 108 to see the field of view (FOV) of the robotic device 102. An eye tracking device 106 may be oriented to face the surgeon 110 and determine a gaze of the surgeon 110 with respect to the display 108 of the robotic device 102. A controller 104, which may be a generic computer such as a laptop or may be a specific controller built into the laparoscope and gaze tracking system, controls the robotic device in response to changes in the gaze point 111 or visual interest of the user. The display 108 may provide an internal view of a portion of the patient's 112 body or other area.

Figure 2:
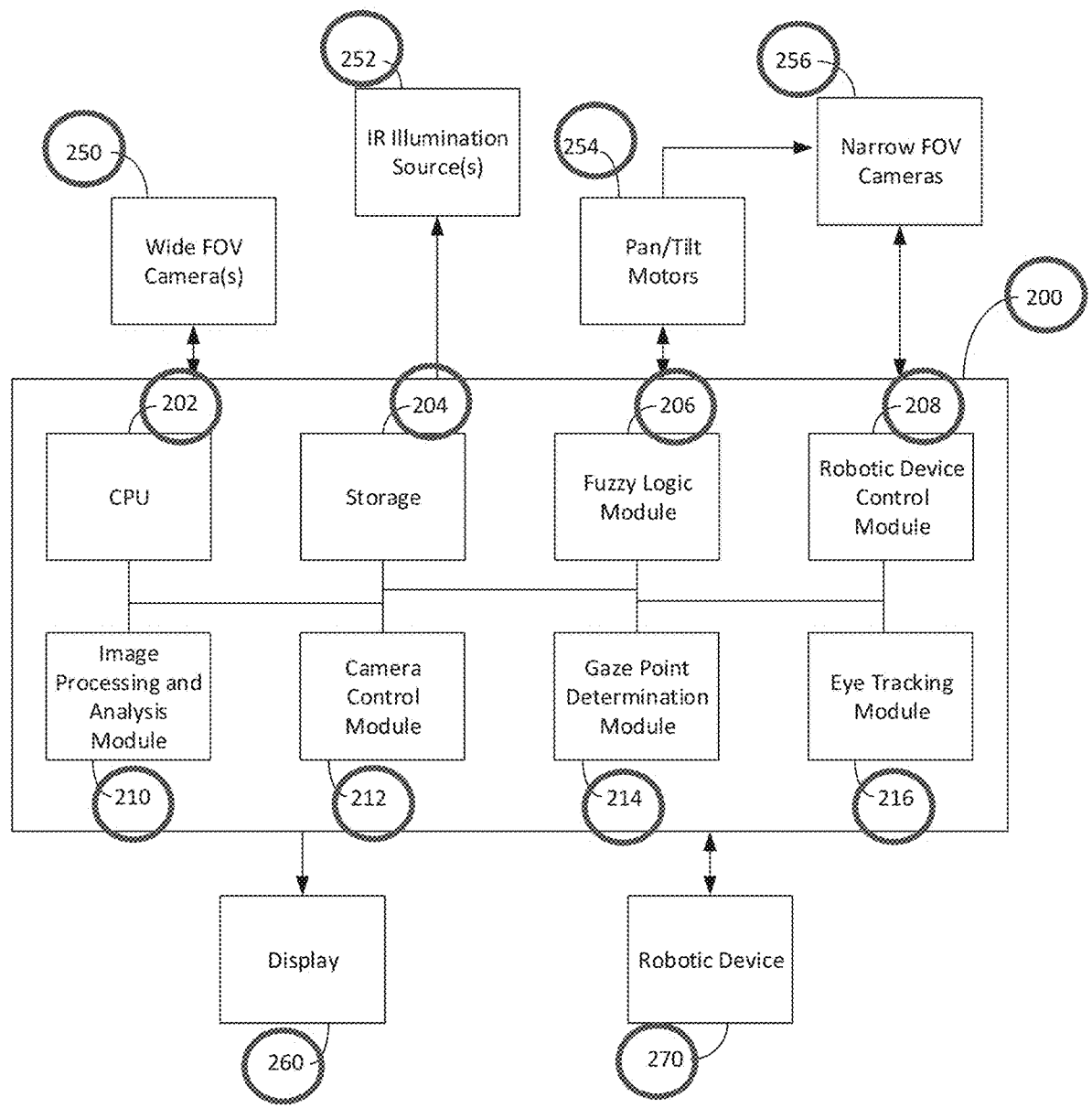
FIG. 2 is a circuit diagram for the gaze detection controller for use in the system of FIG. 1.

Turning now to FIG. 2, is a circuit diagram for the gaze detection controller 200 for the robotic device and system of FIG. 1. The gaze detection controller 200 may have a CPU or processing element 202 for controlling various functions of the controller 200 and may be in electrical communication with other elements of the controller 200. A storage device 204 is provided which may have operation instructions, calibration data, applications for controlling various modules, and the like. An image processing module 210 may input image information from the wide and narrow FOV cameras 250, 256 in order to extract features of the image. The wide camera 250 may be used to detect a user's face (see FIG. 4), while the narrow camera 256 may be used to determine the visual axis of a user's eyes for use with the eye tracking module. Narrow cameras 256 may each be provided with panning and tilting capability, and the gaze detection controller may operate the pan and tilt motors 254 to ensure the narrow cameras 256 are focused on each of the user's eyes, respectively. The gaze detection controller 200 may further control infrared (IR) illumination sources 252 to shine IR light onto the user's eyes. In some examples, more than one IR source is provided, thus projecting a predetermined pattern of reflections or "glints" on the eye.

Figure 7:
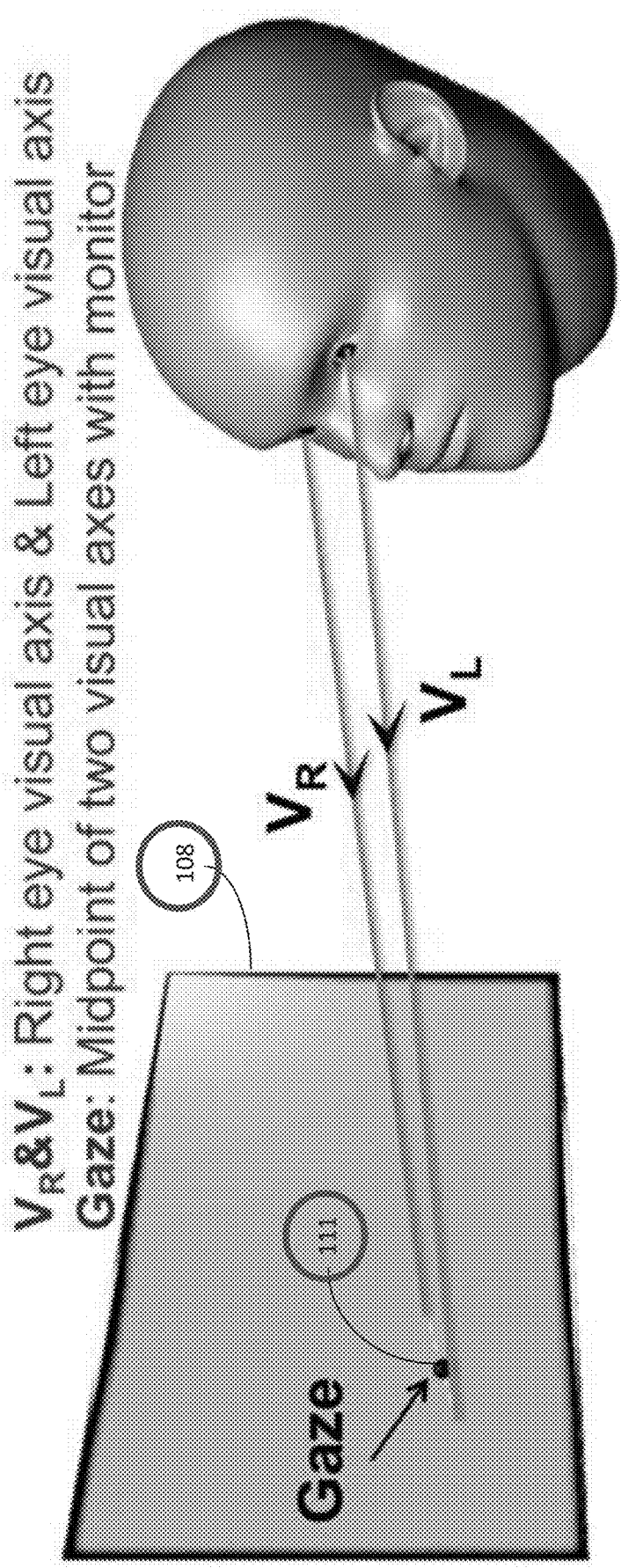
FIG. 7 depicts the respective visual axes of the eyes in relation to a gaze point on a display of the system of FIG. 1.

A gaze point determination module 214, in communication with the eye tracking module 106, may be provided to estimate the gaze point 111 of a user 190 on the display screen 260, which may be the same as the display 108 discussed above in FIG. 1. The gaze point 111 may be the midpoint between the visual axes of the each of the user's eyes, respectively, as shown in FIG. 7. In some examples, the gaze point determination module 214 and eye tracking module 216 may utilize or communicate with the fuzzy logic module 206, which may also be a neural network module, to determine and monitor a visual axis vector for each eye and gaze point 111 location for the user 110.

A robotic device control module 208 may be provided with the gaze detection controller and may be in wired or wireless communication with a robotic device 270, such as a robotic laparoscope or the like. The robotic device control module 208 may also function to transform coordinates of the gaze point 111 on the display screen 108 to movement, articulation, or other control of the robotic device 270. For example, system coordinate transformation achieves intuitive, direct gaze point guidance, where the gaze fixation change on the displayed image is directly transformed as rotational and/or translational motion commands to the robotic laparoscope. Therefore, when a new viewing interest or gaze point 111 is detected, the deviation from the center screen to the position of this new interest indicates the laparoscope's necessary motion information corresponding to the change from its current position. A series of transformations can be expressed as $$_{eyetracker}^{robot}T = {}_{robot\_housing}^{robot}T * {}_{laparoscope}^{robot\_housing}T * {}_{monitor}^{laparoscope}T * {}_{eyetracker}^{monitor}T \quad \text{(Eq. 1)}$$

where $_{eyetracker}^{monitor}T$ is the transformation matrix from the origin of the eye tracker to the origin of the monitor and $_{monitor}^{laparoscope}T$ is the monitor to the origin of the laparoscope image, and $_{robot\_housing}^{robot}T$ is the transformation matrix from the housing linkage 123 to the robot 270 base linkage 125 (the robot kinematics).

In order to convert the image pixel location to laparoscope or other robotic device 270 motion, the transformation matrix $_{laparoscope}^{robot\_housing}T$ is provided. To achieve this transformation relationship, a standard camera calibration is needed for the laparoscope using the Camera Calibration Toolbox in MATLAB. This calibration provides the parameters of the laparoscope, such as camera center and focal length. These parameters, along with the insertion length of the robotic device 270 in the patient's body, build the transformation matrix that converts the image pixels to relative rotation angle and/or translation distance of the robotic device 270 about the patient entry port.

Figure 3:
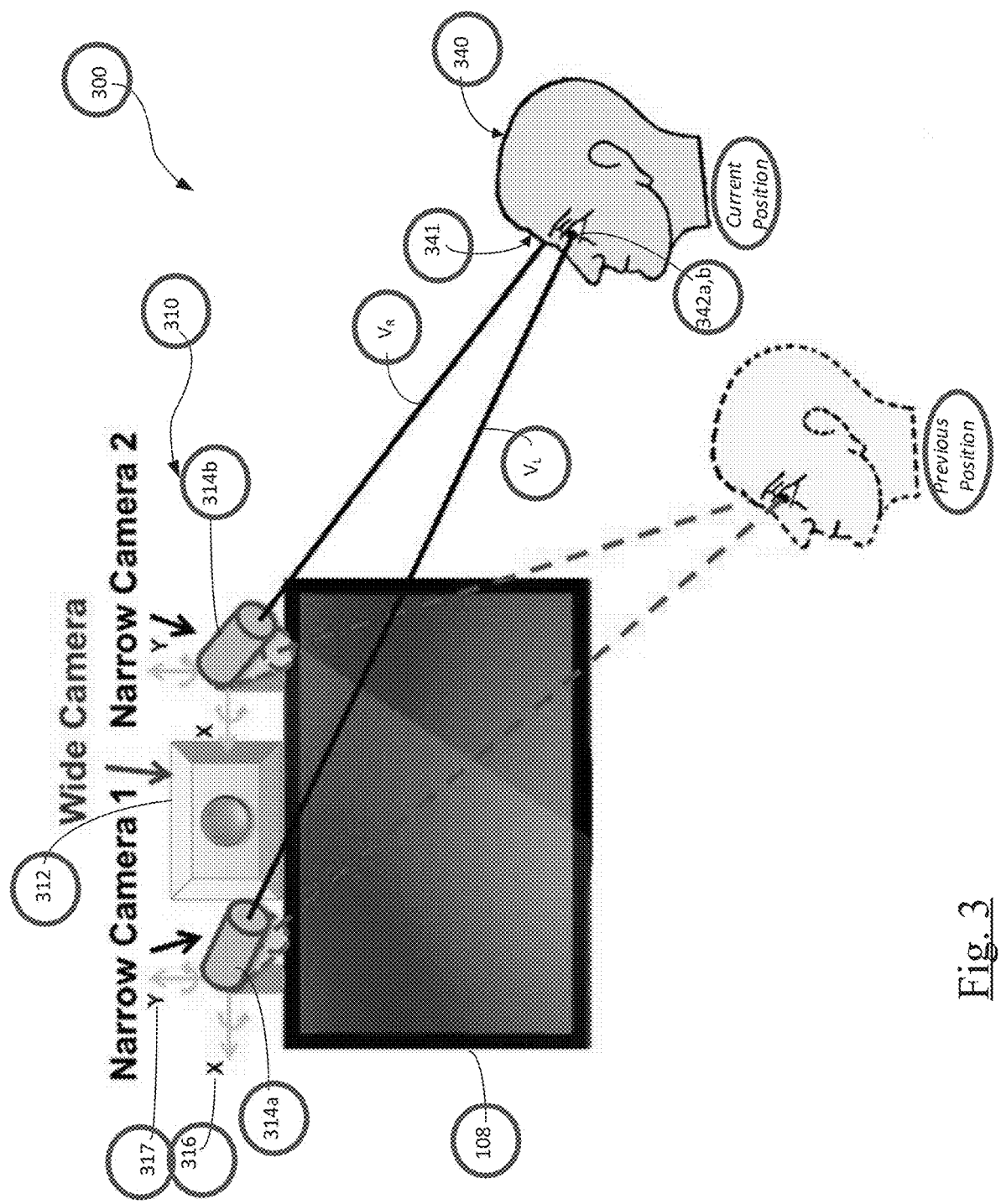
FIG. 3 is an exemplary embodiment of the eye tracking system of FIG. 1.

Turning now to FIG. 3, a more detailed view of the eye tracking device 106 of FIG. 1 is shown. As shown in FIG. 3, a two-tier camera system 310 is provided which has a wide-angle camera 312, or "wide camera," and at least two narrow-FOV cameras 314a,b, or "narrow cameras." A display 330 is shown depicting an output of the cameras 312 and 314a,b. Display 330 is shown to demonstrate the outputs of the cameras 314a, 314b and is not the same as display 108 discussed above in FIG. 1. The wide camera 312 is configured to view a larger area of the room (not shown) in order to keep a user 340 in the wide camera's FOV as the user changes position (see FIG. 3) from a previous position to a current position. The wide camera 312 may cooperate with the image processing module 210 discussed in FIG. 2 to detect a user's face 341 within the field of view (FOV). When a user's face 341 is detected, the location of the eyes 342a,b may be determined and the narrow cameras 314a,b may be panned and tilted to obtain high-resolution, close-up view of the each of the user's eyes 342a,b, respectively. Accordingly, a user 340 may be free to move around the room while the eye tracking device 310 maintains high resolution imagery of the user's eyes.

Figure 4:
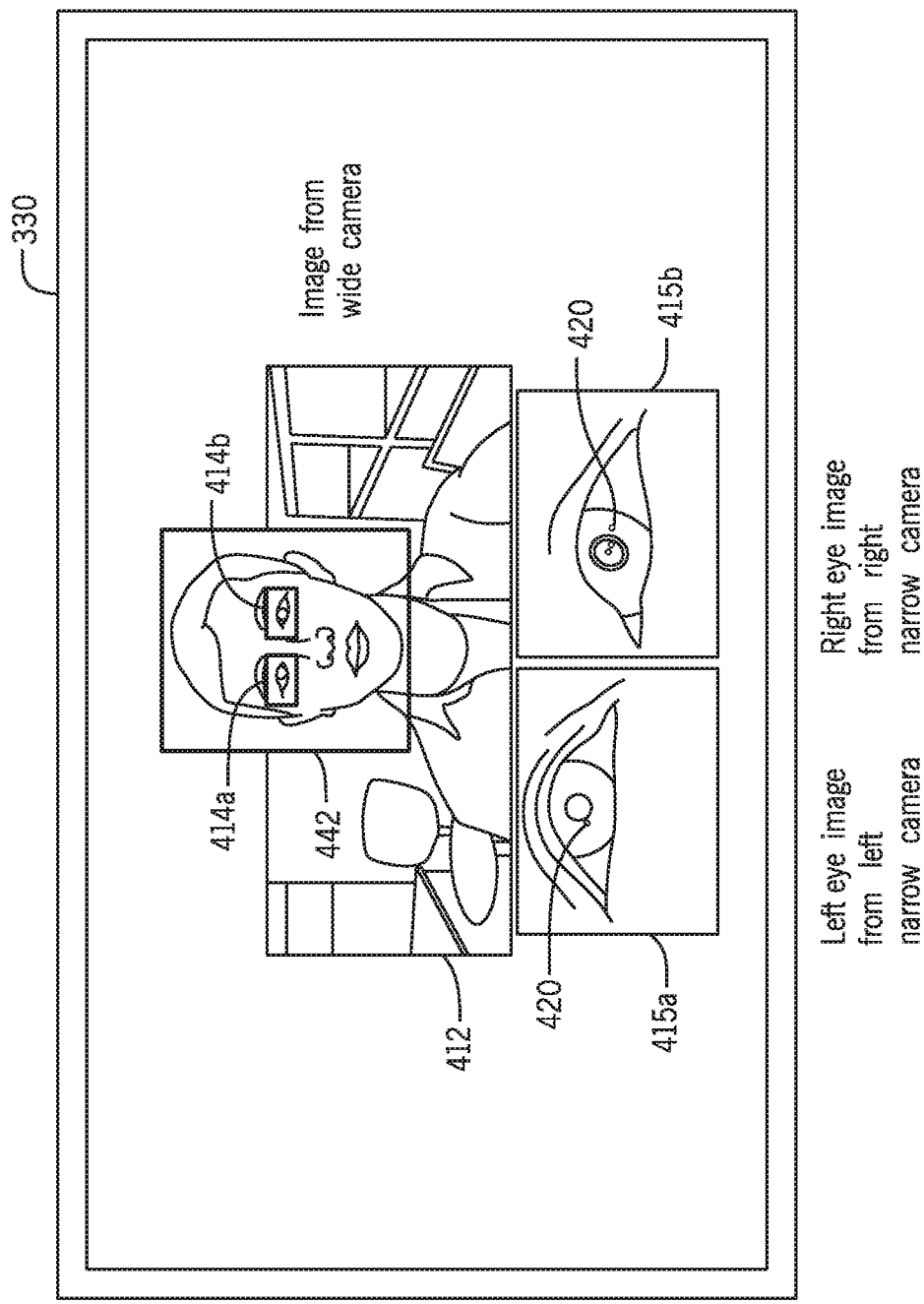
FIG. 4 is an exemplary output of the eye tracking system of FIG. 3, green boxes around eyes, and red box around the face.

FIG. 4 depicts an exemplary view of the outputs 412, 415 of the wide camera 312 and narrow cameras 314. A face area 442 is depicted within the FOV of wide camera 312. Within the face area 442, two eye areas 414 are depicted. The eye areas 414a and 414b substantially correspond to the video outputs 415 a and 415b, respectively. As can be readily seen, the wide camera 312 is capable of tracking a user's face 442 over a wide operating area. The narrow cameras 314 are focused on the user's eyes 342, from which the incident IR light is reflected in a pattern of reflections 420 or "glints."

Figure 5:
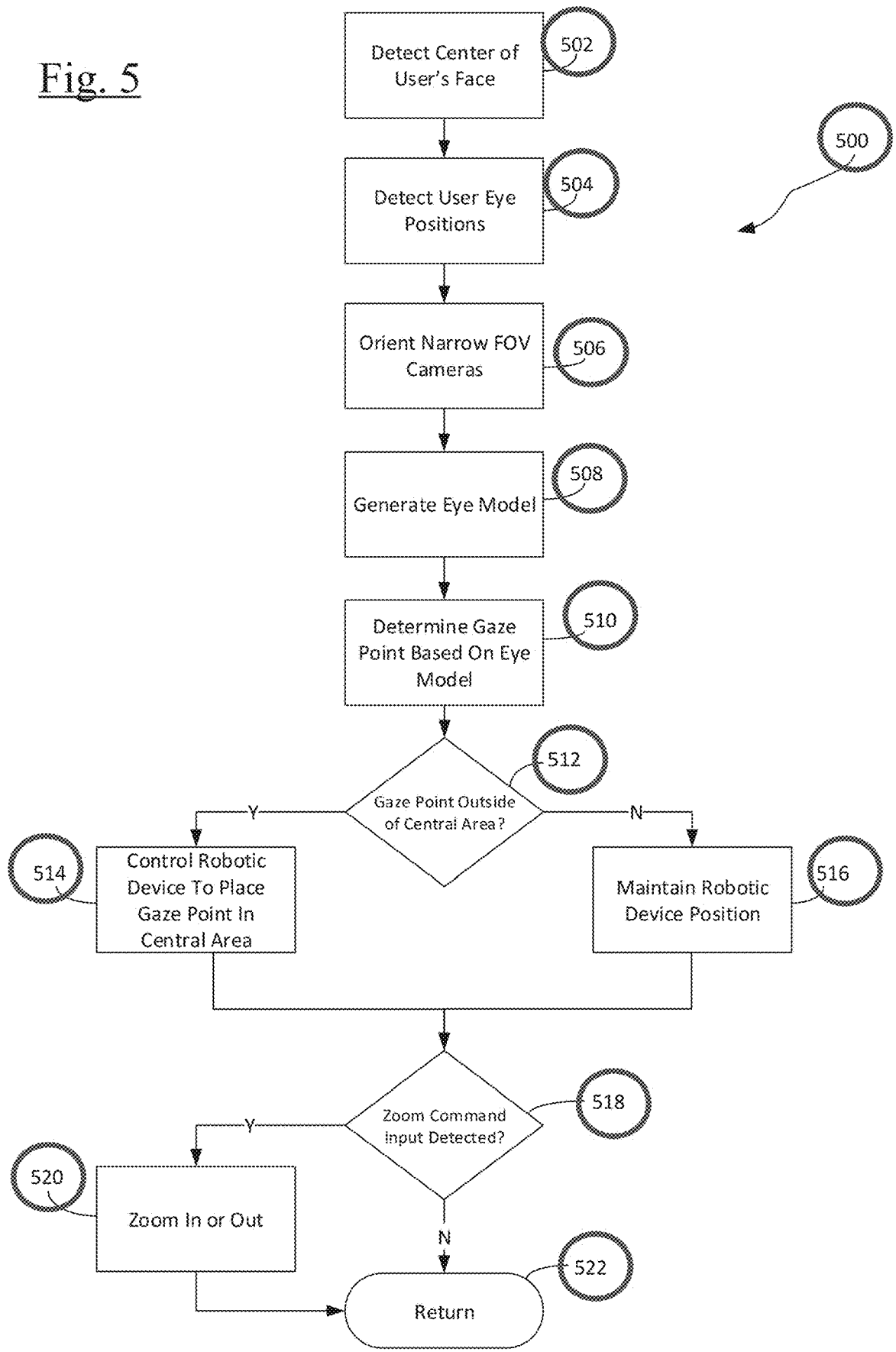
FIG. 5 is a flow diagram for controlling a robotic device such as in the system of FIG. 1.

FIG. 5 is a flowchart for the operation of the robotic control system based on eye tracking. In step 502, the wide camera detects the center of a user's face and proceeds to step 504 to determine the position of each eye of the user. At step 506, the narrow cameras are panned and tilted in order to bring each eye into focus, respectively. The narrow cameras provide a high quality image of the user's eyes, including reflections or "glints" reflected off a user's eyes by the IR illumination devices. After step 506, the method proceeds to step 508 to generate an eye-model based tracking model to determine respective visual axes for each eye, as discussed below with respect to FIGS. 6-7. In step 510, a gaze point on the display is determined based on the eye model generated in step 508, and the intersection of the gaze point with display is determined.

Proceeding to step 512, the gaze detection controller determines if the gaze point is outside of the focus area of the screen, as discussed below with respect to FIGS. 8 and 9. If the gaze point is outside of the focus area, the process proceeds to step 514 wherein the robotic device is controlled to place the gaze point within the focus area of the display screen. If in step 512 the gaze point is not outside the focus area (i.e., the gaze point is within the focus area), then the method proceeds to step 516 to maintain the current robotic device position and field of view.

After steps 514 or 516, the method 500 proceeds to step 518 to determine is a zoom command has be detected by the gaze detection controller. A zoom command is received when a user performs a predetermined task, such as maintaining their gaze at a specified portion of the screen for a predetermined amount of time, which is longer than a predefined dwell time threshold. For example, if the gaze points falls on the boundary of the focus area (the ellipse boundary of the focus area as shown in FIGS. 8-9), the display view will be zoomed out. In some examples, this may cause the camera to be zoomed out therefore the attended site will move to be closer to the center of the new field-of-view. Conversely, if the viewing attention falls at the center of the current field-of-view, the camera will zoom in.

If at step 518 a zoom command is detected, the method proceeds to step 520 to perform the zooming function, after which the process ends at step 522. If at step 518 no zoom command is detected, the process ends at step 522.

It is noted that of the present disclosure may use an eye-model based tracking algorithm to determine the gaze point of a user based on the input of the wide and narrow cameras 316, 314. The advantage of eye-model-based methods is that they do not rely on a pre-calibrated mapping relationship, which effectively solves the recalibration problem when the surgeon's or other user's head moves in activities such as tool changing, communication with other personnel, and checking other monitoring instruments (ultrasound image, heartbeat, blood pressure, etc.). In order to design a remote tracking system with sufficient accuracy, it is crucial to develop an accurate 3-D eye model. To calculate the pupil's center (p), cornea's center (c) and visual axis (V), eye parameters are required, such as the cornea radius (R), the distance from the pupil center (p) to the cornea center (K), refraction index of the cornea (n1) and the deviation angle ($\kappa$), as shown in FIG. 6.

In order to accurately track the gaze point, these parameters need to be estimated accurately (rather than using population averages). A per-user calibration may be performed by having each user observe known points on the monitor. A classic data fitting method, such as a least square algorithm, may be used to estimate the above parameters using the data collected from the calibration step.

Figure 6:
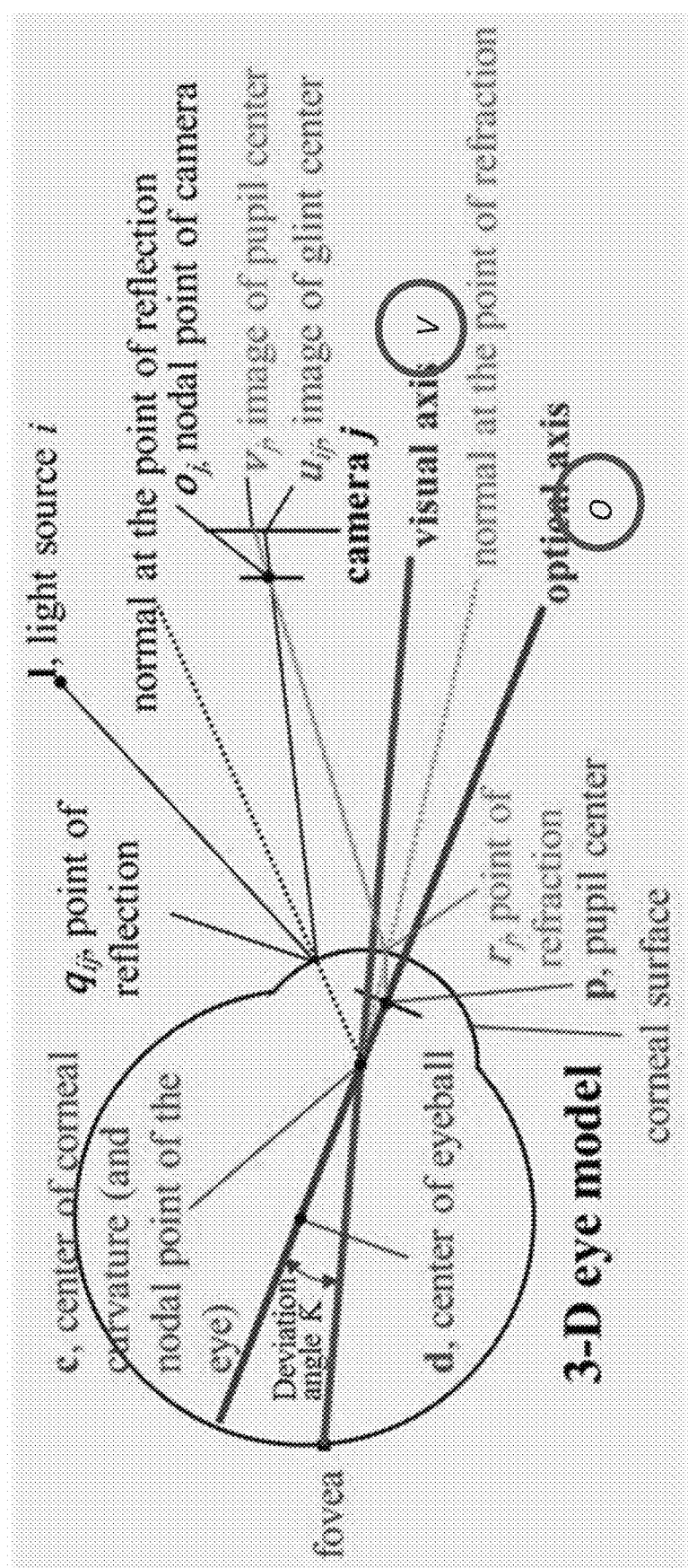
FIG. 6 is an eye-model diagram used for determine the gaze point of a user, blue line is the optical axis and the purple line indicates the visual axis.

Referring to FIGS. 6-7, based on this eye model, the gaze point tracking may include three steps: 1) reconstruct the optical axis (O); 2) calculate the visual axis (V); and 3) determine the gaze point (G). The orientation and location of reflections of lights on the corneal surface and the refraction of the pupil's center through the corneal surface may be used to solve for the absolute positions of the cornea's center and the pupil's center. The optical axis (O) is reconstructed by connecting the pupil's center with the cornea's center. Rotating the optical axis by a deviation angle ($\kappa$), the visual axis (V) is calculated, which is the line connecting the center of the fovea with the nodal point (c) of the eye's optics (FIG. 6). Then, the intersection of the visual axis for each eye ($V_L$, $V_R$ in FIG. 7) with a display screen 108 is used to detect a gaze point 111, as shown in FIGS. 1 and 7. However, due to the error in determining the visual axis for each eye, the respective visual axes may not intersect. In this case, a gaze point 111 may be calculated as the center or midpoint of the two visual axes $V_L$, $V_R$ as they intersect the plane of the display 108.

Figure 8:
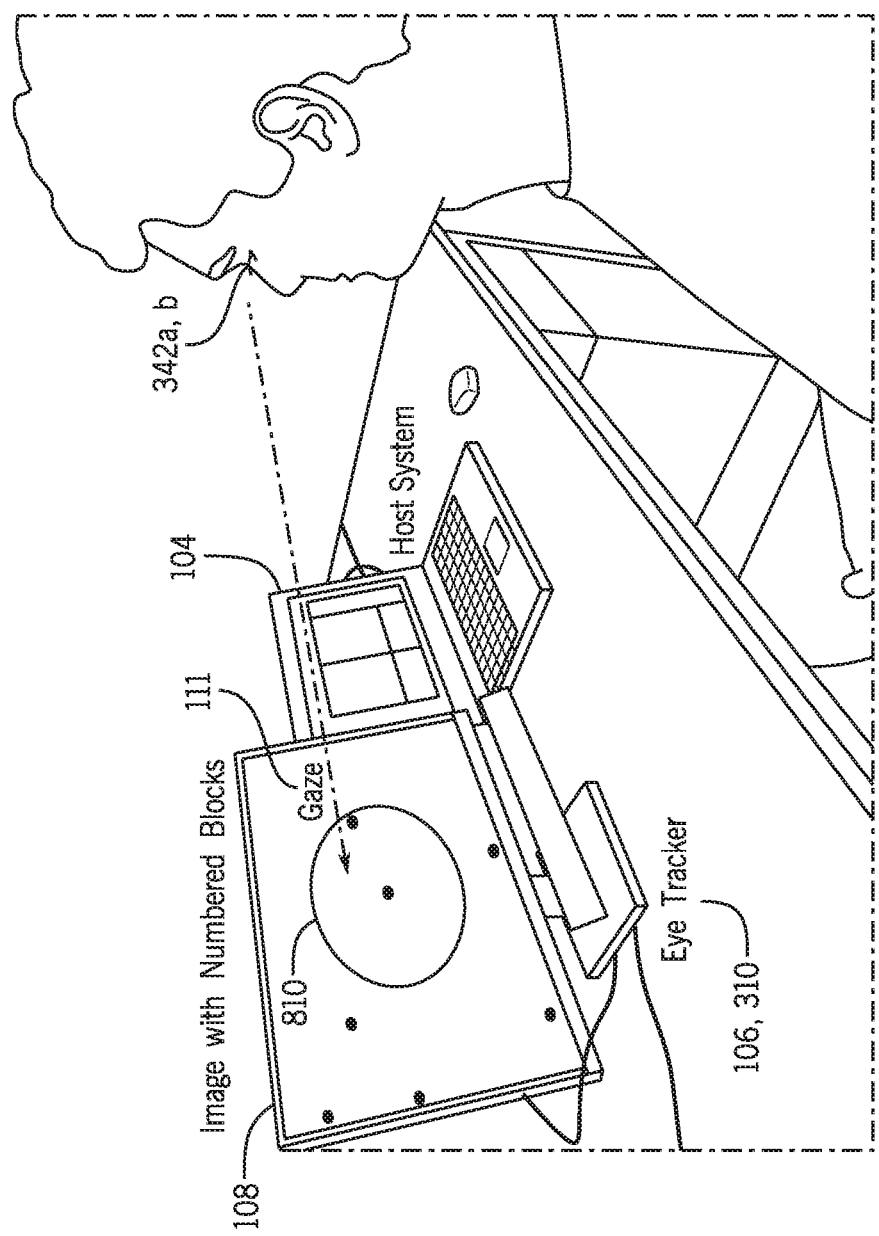
FIG. 8 depicts an exemplary embodiment of the gaze detection system and eye tracker of FIGS. 1 and 3.
Figure 9:
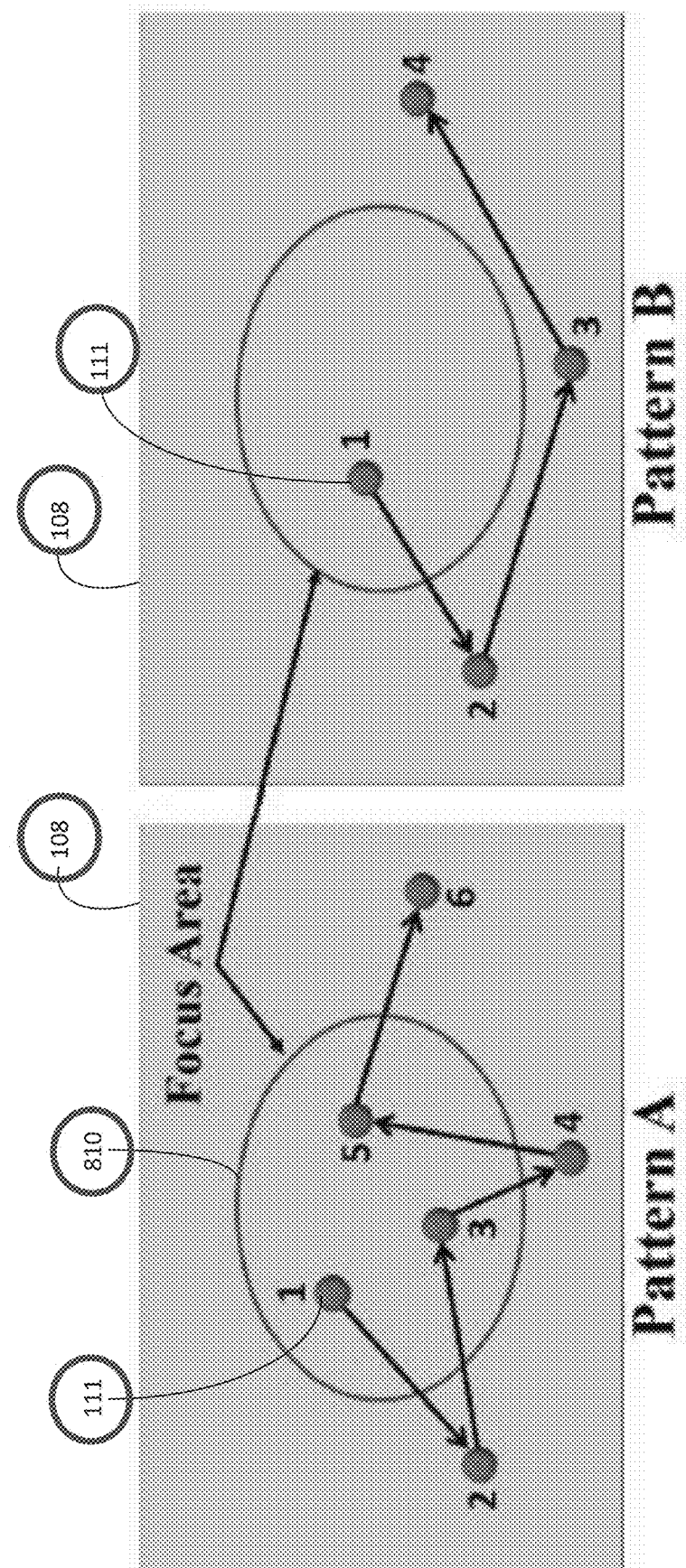
FIG. 9 depicts two patterns of gaze points for use detecting an input command.

As shown in FIGS. 8 and 9, the display 108 may have an elliptical focus area 810 provided in a central portion of the display 108. In some embodiments, the focus area 810 may take up ⅔ of the display screen in a length and height direction. In other embodiments, the focus area 810 may be larger or smaller, and may have substantially any shape. The eye tracking device 106, 310, which may be the same eye tracking device of FIGS. 1 and 3, detects and tracks a user's eyes 342 to determine the gaze point 111 on a screen 108, as discussed above with respect to FIG. 7. If the detected gaze point 111 is within the focus area 810, then the robotic device 102 may remain stationary and not adjust a field of view. However, if the detected gaze point 111 is outside of the focus area 810 with sufficient frequency, it may be determined that a new target or new gaze point 111 is desired and the robotic device 102 may be controlled to change the field of view to match the new target gaze point 111.

For example, in FIG. 9, Pattern A may represent six detected gaze points 111. However, since many gaze points 111 remain within the focus area 810, the gaze detection controller 214 may determine that controlling the robotic device 102 to change the field of view is unnecessary. However, as shown in Pattern B, the first gaze point 111 is within the focus area 810, while subsequent gaze points 111 are outside of the focus area 810. Accordingly, the gaze detection controller 214 may determine that a new point of interest or new target gaze point is desired and may control the robotic device 102 to change the field of view.

A comparison between the presently disclosed gaze-controlled system with existing control systems demonstrates that the presently disclosed devices, methods, and systems result in enhanced intuitiveness and effectiveness of the disclosed devices, methods, and systems. In some examples, the presently-disclosed gaze-guided system may use the controller's eyes to gather input from the field of view, as well as produce output to the field of view. Looking at an object reflects an interest in that object.

The presently disclosed devices, methods, and systems use this link to control the robot, by unobtrusively monitoring the surgeon's gaze movements, and tracking their viewing attention in order to automatically adjust the field of view to match the surgeon's interest. This method may help in reducing or eliminating manual manipulation of the laparoscope from the surgeon's end. The disclosed devices, methods, and systems may help to reduce the learning curve, difficulty, time, and cost of a robotic operation. In many embodiments, the disclosed system may allow for enhanced accuracy in gaze-tracking over a larger workspace.

Analysis of pupillary response and gaze movements on the pattern level may result in three benefits, for example this analysis may enhance the understanding of intention manipulatory gazes, it may help to increase the accuracy and reliability of intent recognition, and may help to improve interaction speed.

Recognition of a surgeon's manipulatory intention using an intelligent fuzzy approach has two benefits: effectively combining correlated gaze features for automated recognition and increased the accuracy and responsiveness of the system.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

We claim:

1. A device for controlling a laparoscope, comprising;
   a first camera for monitoring a user's movement;
   a second narrow-view camera for monitoring a user's left eyeball and pupil of the left eyeball;
   a third narrow-view camera for monitoring the user's right eyeball and pupil of the right eyeball, wherein the second and third cameras can zoom;
   a pan motor and a tilt motor for moving the second camera;
   a pan motor and a tilt motor for moving the third camera;
   a gaze detection controller for receiving signals from the first, second, and third cameras;
   the gaze detection controller comprising a processor for
      analyzing the signal from the first camera to detect and track movement of the user,
      generating a model of the left and the right eyeballs,
      analyzing the signal from the second camera to measure the left eyeball and identify and locate a pupil of the left eyeball to determine from the model a center (p) of the pupil, a center of a cornea (c) and a visual axis (V) of the left eyeball,
      analyzing the signal from the third camera to measure the right eyeball and identify and locate a pupil of the right eyeball to determine from the model a center (p) of the pupil, a center of a cornea (c) and a visual axis (V) of the right eyeball,
   calculating a gaze point from the visual axis of the left eyeball and the right eyeball,
      determining if the gaze point has moved out of a central area relative to a previously calculated gaze point,
      creating a control signal to control a laparascope, and
      outputting the control signal to the laparascope.

2. The device of claim 1, wherein the first camera is a wide-view camera.

3. The device of claim 1, wherein panning, tilting and zooming are in response to a signal from the gaze detection controller.

4. The device of claim 1, wherein one or more input signals from the first and second optical device are analyzed and translated by the gaze detection controller.

5. The device of claim 4, wherein the computing device uses a fuzzy logic algorithm to create an output signal from the input.

6. The device of claim 1, wherein the gaze detection controller transforms coordinates of the gaze point to movement of the laparoscope by
   transforming coordinates of a housing linkage of a robot controlling the laparoscope to coordinates of the robot base linkage.

7. The device of claim 6, wherein the gaze detection controller further transforms coordinates of the gaze point to movement of the laparoscope by
   transforming coordinates of the laparoscope to the coordinates of the robot_housing linkage.

8. The device of claim 7, wherein the gaze detection controller further transforms coordinates of the gaze point to movement of the laparoscope by
   transforming coordinates of a monitor to the coordinates of the laparoscope.

9. The device of claim 8, wherein the gaze detection controller further transforms coordinates of the gaze point to movement of the laparoscope by
   transforming coordinates of the first, second and third cameras to the coordinates of the monitor.

* * * * *